United States Patent
Barrett-Reis et al.

(10) Patent No.: US 6,294,206 B1
(45) Date of Patent: Sep. 25, 2001

(54) POWDERED HUMAN MILK FORTIFIER

(75) Inventors: Bridget Barrett-Reis, Dublin; Patricia A. Reynolds, Columbus; Michael B. Montalto, Upper Arlington; Deborah L. O'Connor, Powell, all of OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/532,838

(22) Filed: Mar. 21, 2000

Related U.S. Application Data

(63) Continuation-in-part of application No. 60/128,575, filed on Apr. 9, 1999.

(51) Int. Cl.$^7$ .............................. A23L 1/302; A23L 1/304; A23C 9/20
(52) U.S. Cl. ................... 426/72; 426/2; 426/73; 426/74; 426/801
(58) Field of Search ................. 426/72, 73, 74, 426/801, 2

(56) References Cited

U.S. PATENT DOCUMENTS

| | | | |
|---|---|---|---|
| 4,692,370 | * | 9/1987 | Grutte et al. ............................ 426/72 |
| 4,753,926 | * | 6/1988 | Lucas ..................................... 426/74 |
| 5,013,569 |   | 5/1991 | Rubin . |
| 6,136,858 | * | 10/2000 | Kuchan et al. ...................... 426/801 |

FOREIGN PATENT DOCUMENTS 0 799 577 A1    10/1997    (EP) .

OTHER PUBLICATIONS

"Dictionnaire vidal", 1990, Editions De Vidal, Paris, XP002144922, p. 100: materna complet.

Tönz, et al., "Die Ernährung kleiner Frühgeborener mit FM$_{85}$: energie–,protein–und mineralienverstärkte Frauenmilch", Monatssschrift Fuer Kinderheilkunde, vol. 134, No. 12, 1986, pp. 885–887, XP000933726.

Moyer–Mileur, et al., "Evaluation of Liquid or Powdered Fortification of Human Milk or Growth and Bone Mineralization Status of Preterm Infants", Journal of Pediatric Gastroenterology and Nutrition, vol. 15, No. 4, 1992, pp. 370–374, XP000933692.

Voyer, et al., "Human Milk Lacto–Engineering: Growth Nitrogen Metabolism, and Energy Balance in Preterm Infants", ACTA Paediatrica Scandinavica, vol. 73, No. 3, 1984, pp. 302–306, XP000933589.

Boehm, "Nitrogen and fat balances in very low birth weight infants fed human milk fortified with human milk or bovine milk protein", European Journal of Pediatrics, vol. 152, No. 3, 1993, pp. 236–239, XP000929747.

Rönnholm, et al., "Human Milk Protein and Medium–Chain Triglyceride Oil Supplementation of Human Milk: Plasma Amino Acids in Very Low–Birth–Weight Infants", Pediatrics, vol. 74, No. 5, 1984, pp. 792–799, XP000933587.

Raschko, et al., "Comparison of Fortified Human Milk (Using Similac Natural Care® With Experimental LBW Infant Formula", Pediatric Research, vol. 21, No. 4, Part 2, 1987, pp. 435A, XP000933586.

Bhatia, et al., "Human Milk Supplementation: Delivery of Energy, Calcium, Phosphorus, Magnesium, Copper, and Zinc", American Journal of Diseases of Children, vol. 142, No. 4, 1988, pp. 445–447, XP000933462.

Mead Johnson & Company, Enfamil Your first choice just got better, LA3012 NEW 10/00, 2000.

Procelli, et al., "Growth in Human Milk–Fed Low Birth Weight Infants Receiving a New Human Milk Fortifier", Annals of Nutrition & Metabolism, 2000, 44:2–10.

Franz, et al., "Prospective Randomized Trial of Early Versus Late Enteral Iron Supplementation in Infants With a Birth Weight of Less Than 1301 Grams", Pediatrics, vol. 106, No. 4, Oct. 2000, pp. 700–706.

Barrett Reis et al., "Enhanced Growth of Preterm Infants Fed a New Powdered Human Milk Fortifier: A Randomized, Controlled Trial", Pediatrics, vol. 106, No. 3, Sep. 2000, pp. 581–588.

Mead Johnson Nutritional Division, Product Handbook Enfamil Human Milk Fortifier, L–B641(8–83).

Schanler, et al., "Fatty Acids Soaps May Be Responsible for Poor Fat Absorption in Premature Infants Fed–Fortified human Milk (FHM)", Abstract No. 1707, Pediatric Research, Apr. 1999, vol. 45, No. 4, pp. 290A.

Schanler, et al., "Postnatal attainment of intrauterine macromineral acceration rates in low birth weight infants fed fortified human milk", The Journal of Pediatrics, Mar. 1995, pp. 441–447.

Porcelli, et al., "A New Human Milk Fortifier (HMF): A Multicenter Report", Pediatric Research, Abstract No. 200, vol. 40, No. 3, 1996.

(List continued on next page.)

*Primary Examiner*—Helen Pratt
(74) *Attorney, Agent, or Firm*—J. Michael Dixon; Nickki L. Parlet

(57) ABSTRACT

The invention relates to a powdered human milk fortifier comprising a protein component typically present in an amount of from about 24 wt/wt % to about 55 wt/wt % of the fortifier powder, and a fat component typically present in an amount of from about 1 wt/wt % to about 30 wt/wt % of the fortifier powder and a carbohydrate component present in a quantity of from about 15 wt/wt % to about 75 wt/wt % of the fortifier powder. Preferably, the powdered human milk fortifier is provided in a unit dose container which holds from about 0.5 gm to about 10 gm of powder. The instant invention also relates to a method of providing nutrition to preterm infants by adding a fortifier powder to human milk and administering the fortified human milk to a premature infant. The invention further provides a method of promoting growth of a premature infant by administering fortified human milk to a premature infant.

13 Claims, No Drawings

OTHER PUBLICATIONS

Schanler, et al., "Fortified Human Milk Improves The Health Of The Premature Infant", Abstract No. 217, Pediatric Research, vol. 40, No. 3, 1996.

Fenton, et al., "Osmolality of Breast Milk Enriched with Added Formula Powders", Abstract No. 1657, Pediatric Research, Apr. 1999, vol. 45, No. 4, p. 281A.

Fenton, et al., "Comparison of Tolerance, Parental Attitudes and Duration of Breast Feeding with Powdered Versus Liquid Breast Milk Enrichment Products for Very Low Birth Weight Infants", Abstract No. 1658, Pediatric Research, Apr. 1999, vol. 45, No. 4, p. 282A.

Sankaran, et al., "A randomized, controlled evaluation of two commercially available human breast milk fortifiers in healthy preterm neonates", Journal of the American Dietetic Associaton, Nov. 1996; 96 : 1145–1149.

McNaught, et al., "An Evaluation of a New Human Milk Fortifier in Preterm Infants", Journal of Investigative Medicine, vol. 48, p. 93A, Jan. 2000.

Lucas, et al., "Randomized outcome trial of human milk fortification and developmental outcome in preterm infants", Am J Clin Nutr 1996; 64 : 142–51.

Barrett–Reis, et al., "An Evaluation of Growth and Serum Biochemistries of Preterm Infants Fed Preterm Human Milk Fortified with a New Powdered Human Milk Fortifier (PHMF)", Abstract 70, Journal of the American College of Nutrition, vol. 18, No. 5, 539, p. 62633, Oct. 1999.

Moro, et al., "Fortificaton of Human Milk: Evaluation of a Novel Fortification Scheme and of a New Fortifier", Journal of Pediatric Gastroenterology and Nutrition, 20:162–172, 1995.

Schanler, et al., "Feeding Strategies for Premature Infants: Benefical Outcomes of Feeding Fortified Human Milk Versus Preterm Formula", Pediatrics, vol. 103, No. 6, Jun. 6, 1999, p. 1150–1157.

Pediatric Nutrition Handbook Fourth Edition, Committee on Nutrition American Academy of Pediatrics, Ronald E. Kleinman, MD, editor, 1998, pp. 55–87.

CRC Handbook of Chemistry and Physics A Ready–Reference Book of Chemical and Physical Data $79^{th}$ Edition, David R. Lide, Ph.D. editor, 1998–1999, pp. 8–111–8–117, 4–35–4–47.

Williams and Chase, Methods in Immunology and Immunochemistry, vol. II, 1968, pp. 280–283.

Ehresmann, et al., "Spectrophotometric Determination of Protein Concentration in Cell Extracts Containing tRNA's and rRNA's", Analytical Biochemistry 54, 454–463 (1973).

Cordle, et al., "Evaluation of the immungenicity of protein hydrolysate formulas using laboratory animal hyperimmunization", Pediatric Allergy Immunol 1994: 5: 14–19.

Meeting the Special Nutrient Needs of Low–Birth–Weight and Premature Infants with Similac® Human Milk Fortifier or Similac Natural Care®, Ross Products Division Abbott Laboratories, Feb. 2000.

Enfamil® Human Milk Fortifier Label, Mead Johnson & Company, 1987.

Enfamil® Human Milk Fortifier Label, Mead Johnson & Company, 2000.

Davies, D.P., "Adequacy of expressed breast milk for early growth preterm infants". Archives of Disease in Childhood, 52, p. 296–301,1997.

Schanler, "Suitability of human milk for the low–birth weight infant", Clinics in Perinatology, 22, pp. 207–222, 1995.

* cited by examiner

POWDERED HUMAN MILK FORTIFIER

CROSS REFERENCE

This application is a continuation-in-part of U.S. patent application Ser. No. 60/128,575 which was filed on Apr. 9, 1999.

TECHNICAL FIELD

The instant invention relates to a powdered human milk fortifier. The instant invention also relates to a method of providing nutrition to preterm infants by adding the fortifier powder to human milk and administering the fortified human milk to a premature infant. The invention further provides a method of promoting growth of a premature infant by administering the fortified human milk to a premature infant. The invention also relates to a method for enhancing the physical stability of human milk by adding an emulsifier to the human milk.

BACKGROUND

Human milk has long been recognized as the ideal feeding for term infants because of its nutritional composition and immunologic benefits. For these reasons, mature donor human milk was considered a desirable feeding for preterm, low-birth-weight (LBW) infants in early newborn intensive care units (NICUs). However, mature donor milk was found not to provide enough of some nutrients to meet rapidly growing LBW infants' needs. There were also concerns about possible bacterial, viral and other contamination of donor milk. For these reasons, milk from the premature infant's own mother has become the preferred feeding in the modern NICU.

Preterm infants are commonly fed either a commercial infant formula designed specifically for these infants or their own mother's milk. Research is still underway regarding the nutritional requirements of these infants. However, numerous studies have documented that unsupplemented preterm milk and banked term milk provide inadequate quantities of several nutrients to meet the needs of these infants (Davies, D. P., "Adequacy of expressed breast milk for early growth of preterm infants". ARCHIVES OF DISEASE IN CHILDHOOD, 52, p. 296–301, 1997). Estimated energy requirements of the growing LBW infant are approximately 120 Cal/kg/day. Exact energy needs vary among infants because of differences in activity, basal energy expenditure, the efficiency of nutrient absorption, illness and the ability to utilize energy for tissue synthesis. At 120 Cal/kg/day, about 50% of the energy intake of an LBW infant is expended for basal metabolic needs, activity and maintenance of body temperature. About 12.5% is used to synthesize new tissue, and 25% is stored. The remaining 12.5% is excreted. Mature preterm human milk is estimated to contain about 67 Cal/100 ml. To achieve an intake of 120 Cal/kg/day, a LBW infant needs to consume about 180 ml of preterm milk/kg/day. This feeding volume is often not well tolerated. Volumes of 100 to 150 milkg/day are typically fed. Therefore, to achieve an intake of 120 Cal/kg/day in an acceptable volume, the caloric content of preterm milk must be supplemented.

Additionally, relative to estimates of the infant's requirements, preterm human milk is lacking in calcium, phosphorus and protein. When preterm human milk is fortified with protein and energy, a LBW infant's growth approaches that occurring in utero. Additionally, when fortified with calcium and phosphorus, there is increase accretion of these minerals and improvement of bone density. Thus, it has been recommended that when preterm infants are fed preterm human milk, the human milk be fortified to better meet the nutritional needs of the preterm infant.

Liquid and powder forms of preterm milk fortifiers have been marketed domestically in response to this recognized need. The energy and nutrient composition for a typical days supplement of commercially available powder and liquid human milk fortifiers are presented in Table 1.

TABLE 1

Energy and Nutrient Composition of Human Milk Fortifiers

| Nutrients | Enfamil ® Human Milk Fortifier Powder (3.8 g) | Similac Natural Care ® Liquid (100 ml) |
|---|---|---|
| Energy, Kcal | 14 | 81 |
| Protein, gm | 0.7 | 2.2 |
| source | whey protein concentrate, sodium caseinate | nonfat milk, whey protein concentrate |
| Fat, gm | <0.1 | 4.4 |
| source | none added | MCT, soy, coconut |
| Carbohydrate, gm | 2.7 | 8.6 |
| source | corn syrup solids | corn syrup solids, lactose |
| Minerals | | |
| calcium, mg | 90 | 171 |
| phosphorus, mg | 45 | 94 |
| magnesium, mg | 1 | 10 |
| zinc, mg | 0.71 | 1.22 |
| manganese, mcg | 4.7 | 9.8 |
| copper, mg | 0.06 | 0.2 |
| sodium, mg | 7 | 35 |
| potassium, mg | 15.6 | 105 |
| chloride, mg | 17.7 | 66 |
| iron, mg | none added | 0.3 |
| selenium, mcg | none added | 1.46 |
| Vitamins | | |
| A, IU | 950 | 1,008 |
| D, IU | 210 | 122 |
| E, IU | 4.6 | 3.2 |
| K, mcg | 4.4 | 10 |
| Thiamin, mg | 0.15 | 0.2 |
| Riboflavin, mg | 0.21 | 0.5 |
| B6, mg | 0.11 | 0.2 |
| B12, mcg | 0.18 | 0.45 |
| Niacin, mg | 3 | 4 |
| Folic acid, mcg | 25 | 30 |
| Pantothenic acid, mg | 0.73 | 1.54 |
| Biotin, mcg | 2.7 | 30 |
| C, mg | 11.6 | 30 |

Enfamil ® Human Milk Fortifier (Mead Johnson Nutritionals, Evansville, Ind.) Values are label claim for 4 packets which is added to 100 ml of mother's milk.
Similac Natural Care ® (Ross Products Division of Abbott Laboratories, Chicago, ILL.) Values are label claim for 100 ml.

Similac Natural Care® and Enfamil® Human Milk Fortifier are commercially available human milk fortifiers. The fortifiers differ with respect to their form, source of ingredients and energy and nutrient composition. There is need in the NICU for both liquid and powdered human milk fortifiers. Powder products are advantageous to minimize the dilution of mother's milk. For example, dilution of mother's milk is undesirable when a mom is able to produce and pump sufficient milk to meet the volume needs of her infant, However, if mom's milk supply is limited, a liquid fortifier may be used to stretch her supply of human milk. Similac Natural Care® is designed to be added to preterm milk in a one-to-one ratio or fed alternately with human milk meeting a need in the NICU.

Generally, premature infants stay in the NICU for several weeks after their mother has been released from the hospital.

These tiny infants can easily be held in the palm of an adult hand. They are usually placed in special incubators; they are on respirators to assist in their breathing; they have several indwelling catheters for administration and/or withdrawal of fluid samples; and are intubated for tube feeding.

The method of enteral feeding chosen for each infant is based on gestational age, birth weight, clinical condition and experience of the hospital nursing personnel. Specific feeding decisions that are made by the clinician include age to initiate feeding, route of feeding delivery, feeding frequency, strength of feeding, and rate of advancement. The route for enteral feeding is determined by the infant's ability to coordinate sucking, swallowing, and breathing, which appear at approximately 32 to 34 weeks' gestation. Preterm infants of this gestational age who are alert and vigorous may be fed by nipple. Infants who are less mature, weak, or critically ill require feeding by tube to avoid the risk of aspiration and to conserve energy. Nasogastric and orogastric feedings, the most commonly used tube feedings in the neonatal intensive care unit, may be accomplished with bolus or continuous infusions of fortified human milk. Infants who receive nasogastric or orogastric feedings may be fed on an intermittent bolus or continuous schedule. Intermittent feedings every 2 to 3 hours simulate the pattern of feeding the infant will have when advanced to bottle feeding or breast feeding. Continuous feedings may be better tolerated by very small infants, infants who previously have not tolerated bolus feedings and infants in whom clinically significant malabsorption develops with bolus feedings. However, reduced nutrient delivery is a problem associated with continuous feeding. Fat from human milk tends to adhere to the feeding tube surfaces and reduce energy density. Likewise, the loss of nutrients for fortifiers used to supplement human milk is increased when given in a continuous feeding.

In order to continue feeding the infants their own mother's milk after their mother's discharge from the hospital, the mother must express milk at home into suitable containers, store the milk in the refrigerator or freezer and transport the expressed milk to the NICU. Once at the NICU, the milk is stored in refrigerator or freezer temperatures depending on the milk volume required for feeding that day. Typically, the amount of milk that will be fed to the infant within 24 hours after being expressed is refrigerated. The extra expressed milk is frozen. Consequently, the expressed milk may be subjected to several different storage conditions prior to preparation as a days feeding.

Human milk fortification is generally used for all infants who require tube feeding of human milk and for a few infants who require fluid restriction. Typical feeding protocols for premature infants (<1500 g) include the addition of fortifier once the infant is receiving unfortified human milk at approximately 100 ml/kg/day. The fortifier is added at half dose initially. For example, two 0.96 gm packets of Enfamil® Human Milk Fortifier is added to 100 ml of mother's milk. If the infant tolerates the fortified milk for 24 hours, the fortifier is increased to full dose. In the case of the example above, the fortifier is increased to four 0.96 gm packets in 100 ml of mother's milk.

Typically, the amount of human milk prepared is based on the amount of milk needed to provide the infant with a 24-hour supply. For example, a 1500 gm infant would be fed 150 ml of milk a day. If frozen milk is used, the frozen milk is placed in a warm water bath until completely thawed. Special attention is given to mixing in the fortifiers. Gentle mixing is required to avoid breaking the milk fat globule, which can increase the adherence of the milk fat to the sides of feeding containers and result in significant loss of fat (energy). The prescribed amount of fortified milk is drawn up into syringes and labeled with identification. When milk preparation is complete, the labeled, aliquoted feedings are delivered to the nurseries and placed into refrigerators for easy access by the nursing staff. Typically, the refrigerated fortified milk is warmed prior to feeding. For example, the fortified milk is warmed in a dry heat laboratory incubator set within a range of 35–45° C. for a maximum of 15 minutes. This brings the temperature of the fortified milk to room temperature. The fortified milk may be administered to the infant as a bolus feeding or through a syringe infusion pump for continuous feeding. If an infusion pump is used, the syringe tip is positioned upright to allow for a continuous infusion of fat and the syringe is attached directly to the feeding tube to decrease the potential surface area that the fat and immunologic components may adhere to. The primary advantage of the powdered fortifier is that there is minimal dilution of human milk. There is currently only one powdered human milk fortifier available on the domestic market (Enfamil® Human Milk Fortifier). Four packets of Enfamil® Human Milk Fortifier powder (0.96 g powder/packet) is added to 100 mL of preterm milk. A study in preterm infants receiving this powdered fortifier demonstrated poor fat absorption (Schanler, "Suitability of human milk for the low-birth weight infant", CLINICS IN PERINATOLOGY, 22, pp. 207–222, 1995). Poor fat absorption negatively impacts the growth in these premature infants. In addition, reports from the NICUs described a residue that clung to the walls of the reconstitution container when the commercially available fortifier powder was added to human milk and there were concerns that the infants were not actually receiving all the nutrients in the fortified milk.

There is a need for a powdered human milk fortifier which is well tolerated by preterm infants and which demonstrates good fat absorption to provide much needed energy to the preterm infant. Additionally, there is a need for a powdered human milk fortifier that reconstitutes well in human milk so that all of the nutrients are actually delivered to the preterm infant. Further, there is a need for a method of preventing the human milk emulsion from breaking and causing the fat to cling to the syringe and feeding tube thereby under delivering much needed energy calories.

The instant invention is a powdered human milk fortifier that promotes the physical stability of the fortified human milk admixture. Further, the powdered human milk fortifier of the instant invention is well tolerated and maximizes the health benefits of human milk while addressing the variability of human milk as a sole source of energy, protein, calcium, phosphorus, sodium and other micronutrients.

SUMMARY OF THE INVENTION

Relative to estimates of the low birth weight (LBW) infant's requirements, human preterm human milk is lacking in calcium, phosphorus, energy and protein. When preterm human milk is fortified with protein and energy, a LBW infant's growth approaches that occurring in utero. Additionally, when fortified with calcium and phosphorus, there is increase accretion of these minerals and improvement of bone density. Thus, it has been recommended that when preterm infants are fed preterm human milk, the human milk be fortified to better meet the nutritional needs of the preterm infant.

The fortifier powder of the instant invention improves upon the prior art fortifier powder by providing higher amounts of protein and fat in the fortifier powder thereby improving the growth patterns of preterm infants when compared to infants fed the prior art fortifier powder. Protein precipitation issues of the prior art fortifier powder have also been successfully addressed through the addition of insoluble calcium which surprisingly did not negatively impact the bone development of these premature infants. Further, the addition of the small amount of emulsifier in the fortifier powder of the instant invention to human milk surprisingly improved the emulsion stability of the fortified human milk.

The instant invention generally relates to a powdered human milk fortifier which typically includes a protein component present in a quantity of from about 24 wt/wt % to about 55 wt/wt % of the fortifier powder, a fat component present in a quantity of from about 1 wt/wt % to about 30 wt/wt % of the fortifier powder and a carbohydrate component present in a quantity of from about 15 wt/wt % to about 75 wt/wt % of the fortifier powder.

Milk fat globules of human milk are known to separate from the milk and adhere to the sides of feeding containers which result in significant loss of fat, a major source of energy for the infant. An emulsifier not only helped the water soluble and insoluble components of the fortifier powder to incorporate into the human milk, it surprisingly helped to prevent phase separation of expressed human milk. Typically, an emulsifier is present in the fortifier powder in a quantity of from about 1 wt/wt % to about 10 wt/wt % of the fat component which corresponds with 0.1 wt/wt % to about 1 wt/wt % of the fortifier powder.

Small volumes of fortified human milk (25 ml to 100 ml) are prepared for a days feeding of a premature infant. Consequently, a bulk container of fortifier powder would be repeatedly opened, powder scooped out, recovered and stored which generates concerns about powder sterility in a hospital environment. Individual unit doses allow for addition of small amounts of powder to human milk without the possibility of contamination of the remaining powder since all of the powder is used in a single preparation. Preferably, the fortifier powder is provided in individual unit dose containers which holds from about 0.5 gm to about 10 gm of the fortifier powder.

The instant invention also relates to a method of providing nutrition to preterm infants by adding the fortifier powder to human milk and administering the fortified human milk to a premature infant. The invention further provides a method of promoting growth of a premature infant by administering the fortified human milk to a premature infant.

The invention also relates to a method for enhancing the emulsion stability of human milk by adding an emulsifier to the human milk.

DETAILED DESCRIPTION OF THE INVENTION

As Used Herein:

The terms "premature", "preterm" and "low-birth-weight (LBW)" infants are used interchangeably and refer to infants born less than 37 weeks gestational age and/or with birth weights less than 2500 gm.

"A unit dose" refers to individual packages of fortifier powder containing an amount of fortifier powder that will be used in a preparation. There will be no leftover fortifier powder requiring storage. The amount of fortified human milk prepared for a premature infant typically ranges from 25 ml to 150 ml a day. Consequently, a single unit dose is the appropriate amount of powder to fortify a 25 ml preparation. Multiple packages are added to the larger volume preparations.

The term "growth" refers to gains in weight, length and/or head circumference.

The term "insoluble calcium" refers to food grade calcium sources listed in the CRC HANDBOOK OF CHEMISTRY AND PHYSICS as sparingly soluble in water.

The term "vitamin E" refers to a group of tocopherols that differ only in the number and position of methyl groups on the ring. The most active form of vitamin E, is also the most widely distributed in nature. When tocopherol was first synthesized, the synthetic material was found to have a slightly lower biological activity than the tocopherol from plants. Because of this phenomena, the natural occurring form has been designated RRR-"-tocopherol. For dietary purposes, vitamin E activity is expressed as RRR-"-tocopherol equivalents (TEs). One TE is the activity of 1 mg of RRR-"-tocopherol. One mg of RRR-"-tocopherol is equivalent to 1.49 IU of vitamin E.

"Maltodextrins" and "corn syrups" refer to complex carbohydrates routinely used in nutritional formulations because of their excellent digestibility and functional properties. Specifically, they are good water binders and provide products with desired texture and mouth feel. Maltodextrins are polysaccharides obtained from the acid or enzyme hydrolysis of corn starch. Their classification is based on the degree of hydrolysis and is reported as "dextrose equivalence (DE)". The FDA defines maltodextrins as non-sweet, nutritive polysaccharides that have a DE less than 20. Corn syrup solids are defined as having DE's greater than 20. Corn syrup solids consist of dextrose chains about 3 to 4 units long while maltodextrins are less hydrolyzed and contain longer dextrose chains. The difference in polymer length results in different functionality, viscosity, mouth feel and osmolality.

It is a principal object of the invention to provide an improved powdered human milk fortifier for premature infants who require additional nutrients to support their growth. The invention is a powder which when added to human milk supplements the levels of protein, fat, vitamins and minerals. Another object of this invention is to provide a method for providing supplemental nutrients to a premature infant who requires additional nutrients for growth.

Although not intended to limit the invention in any manner, but to merely serve as a general guideline, the fortifier powder of this invention will typically provide the following macronutrient distribution. The protein component will typically be present in an amount of from about 24 wt/wt % to about 55 wt/wt % of the fortifier powder, preferably from about 25 wt/wt % to about 42 wt/wt % of the fortifier powder, more preferably from about 28 wt/wt % to about 36 wt/wt % of the fortifier powder. The fat component will typically be present in an amount of from about 1 wt/wt % to about 30 wt/wt % of the fortifier powder, preferably from about 5 wt/wt % to about 20 wt/wt % of the fortifier powder, more preferably from about 8 wt/wt % to about 18 wt/wt % of the fortifier powder. The carbohydrate component will typically be present in an amount of from about 15 wt/wt % to about 75 wt/wt % of the fortifier powder, preferably from about 38 wt/wt % to about 70 wt/wt % of the fortifier powder, more preferably from about 46 wt/wt % to about 64 wt/wt % of the fortifier powder. Additionally, the amount of powder required to provide a unit dose of the fortifier will typically range from about 0.5 gm to about 10 gm of powder in a unit dose, preferably from about 0.8 gm to about 5.0 gm of powder in a unit dose, more preferably from about 0.85 gm to about 2.0 gm of powder in a unit dose. The caloric density is typically from about 1.0 kcal/gm powder to about 8.5 kcal/gm powder.

The first component of the fortifier powder of this invention is a source of protein. Protein is needed for growth, synthesis of enzymes and hormones, and replacement of protein lost from the skin and in urine and feces. These metabolic processes determine the need for both the total amount of protein in a feeding and the relative amounts of specific amino acids. The adequacy of the amount and type of protein in a feeding for infants is determined by measuring growth, nitrogen absorption and retention, plasma amino acids, certain blood analytes and metabolic responses.

As stated above, the protein component will typically be present in an amount of from about 24 wt/wt % to about 55 wt/wt % of the fortifier powder. The proteins that may be utilized in the nutritional products of the invention include any proteins or nitrogen source suitable for human consumption. Such proteins are well known by those skilled in the art and can be readily selected when preparing such products. Examples of suitable protein sources for a premature infant typically include casein, whey, condensed skim milk, nonfat milk, soy, pea, rice, corn, hydrolyzed protein, free amino acids, protein sources which contain calcium in a colloidal suspension with the protein and mixtures thereof.

The preferred protein source will typically be comprised of about 51 wt/wt % of the protein component as whey protein concentrate and about 49 wt/wt % of the protein component as nonfat dry milk which corresponds to about 60 wt/wt % of the protein component as whey and about 40 wt/wt % of the protein component as casein.

Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Mo.

The second component of the fortifier powder of this invention is a source of fat. Fat is an ideal source of energy for LBW infants, not only because of its high caloric density but also because of its low osmotic activity in solution.

As stated above, the fat component will typically be present in an amount of from about 1 wt/wt % to about 30 wt/wt % of the fortifier powder. Examples of suitable fat sources typically include high oleic safflower oil, soy oil, fractionated coconut oil (medium chain triglycerides, MCT oil), high oleic sunflower oil, corn oil, canola oil, coconut, palm and palm kernel oils, marine oil, cottonseed oil and specific fatty acids such as docosahexaenoic acid and arachidonic acid.

Docosahexaenoic acid (DHA) is an omega-3 fatty acid and is thought to be essential for the proper brain and vision development of infants because it is the most abundant long chain polyunsaturated fatty acid (PUFA) in the brain and retina. Although a metabolic pathway exists in mammals for the biosynthesis of DHA from dietary linolenic acid, this pathway is bioenergetically unfavorable and mammals are thought to obtain most of their DHA from dietary sources. In the case of infants, the most likely source would be human milk. Indeed, DHA is the most abundant 20 carbon omega-3 PUFA in human milk. However, human milk DHA content will vary greatly depending on the diet of the mother. If the mother eats fish high in DHA often, her milk will contain higher DHA levels, while a mom with less access to fish will have lower DHA levels in her milk. Consequently, human milk may require DHA supplementation to insure that the preterm infant is receiving sufficient amounts of DHA. Preferably, DHA supplementation is accompanied by arachidonic acid supplementation. U.S. Pat. No. 5,492,938 to Kyle et al. describes a method of obtaining DHA from dinoflagellates and its use in pharmaceutical composition and dietary supplements.

Typically, MCT oil is the preferred fat source which comprises 100% of the fat component. This fat source at this level provides well tolerated fat calories to the premature infant in addition to providing a vehicle for fat soluble vitamins and emulsifiers.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Sunflower and cottonseed oils are available from Cargil of Minneapolis, Minn. Safflower oil is available from California Oils Corporation of Richmond, Calif. DHA is available from Martek Biosciences Corporation of Columbia, Md. Arachidonic acid is available from Genzyme Corporation of Cambridge, Mass.

An emulsifier is typically incorporated into the fortifier powder. Emulsifiers help the water soluble and insoluble components of the fortifier powder incorporate into the human milk. Examples of suitable emulsifiers typically include soya bean lecithin, polyoxythylene stearate, polyoxyethylene sorbitan mono-oleate, polyoxyethylene sorbitan monopalmitate, polyoxyethylene sorbitan monostearate, ammonium phosphatides, polyoxyethylene sorbitan monolaurate, citric acid esters of mono and diglycerides of fatty acids, tartaric acid esters of mono and diglycerides of fatty acids.

The preferred emulsifier source is natural soy lecithin. The amount of emulsifier will typically be present in an amount of from about 1 wt/wt % to about 10 wt/wt % of the fat component which corresponds to about 0.1 wt/wt % to about 1 wt/wt % of the fortifier powder. Preferably the emulsifier is present in an amount of from about 1.5 wt/wt % to about 5 wt/wt % of the fat component.

Numerous commercial sources for the emulsifiers listed above are readily available and known to one practicing the art. For example, soya bean lecithin is available from Archer Daniels Midland Company in Decatur, Ill. Polyoxythylene stearate, polyoxyethylene sorbitan mono-oleate, polyoxyethylene sorbitan monopalmitate, polyoxyethylene sorbitan monostearate, polyoxyethylene sorbitan monolaurate, citric acid esters of mono and diglycerides of fatty acids, and tartaric acid esters of mono and diglycerides of fatty acids are available from Quest in Owings Mills, Md.

The third component of the fortifier powder of this invention is a source of carbohydrates. Carbohydrate is a major source of readily available energy that the LBW infant needs for growth and that protects the infant from tissue catabolism. In human milk and most standard milk-based infant formulas, the carbohydrate is lactose. LBW infants may be unable to fully digest lactose because lactase activity in the fetal intestine is not fully developed until late in gestation (36 to 40 weeks). On the other hand, sucrase activity is maximal by 32 weeks' gestation, and glucosoamylase activity, which digests corn syrup solids (glucose polymers), increase twice as rapidly as lactase activity during the third trimester.

As noted above, the carbohydrates will typically be present in an amount of from about 15 wt/wt % to about 75 wt/wt % of the fortifier powder. The preferred carbohydrate level and source is selected to decrease osmolality and viscosity of the reconstituted product. The preferred carbohydrate source is 100% of the carbohydrate component as corn syrup.

The carbohydrates that may be used in the fortifier powder can vary widely. Examples of carbohydrates suitable for preterm infants typically include hydrolyzed corn starch, maltodextrin, glucose polymers, sucrose, corn syrup, corn syrup solids, rice syrup, glucose, fructose, lactose, high fructose corn syrup and indigestible oligosaccharides such as fructooligosaccharides (FOS). Any single carbohydrate listed above, or any combination thereof, as appropriate may be utilized.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minn., Minnesota. Fructose is available from A. E. Staley in Decatur, Ill. Maltodextrin, glucose polymers, hydrolyzed corn starch are available from American Maize Products in Hammond, Ind. Sucrose is available from Domino Sugar Corp. in New York, N.Y. Lactose is available from Foremost in Baraboo, Wis. and indigestible oligosaccharides such as FOS are available from Golden Technologies Company of Golden, Colo.

The osmolality of the fortified human milk plays an important role in the infants tolerance of their feedings such as abdominal distention and vomiting/spit-up. Osmolality of the fortified human milk is tied to the level and source of carbohydrate utilized in the fortifier powder. The osmolality of the fortifier powder of the instant invention reconstituted in human milk is typically less than about 400 mOsm/kg water, preferably from about 300 mOsm/kg water to about 400 mOsm/kg water. The substitution of fat for some of the carbohydrate in the fortifier powder of the instant invention serves to reduce the osmolality of fortified human milk by replacing the carbohydrate which has a high osmotic activity with fat which has a low osmotic activity. The type of carbohydrate incorporated into the fortifier powder also impacts the osmolality of the fortified human milk. The more hydrolyzed the carbohydrate source (higher DE) the higher the osmotic activity. Additionally, partially hydrolyzed carbohydrate sources may further increase the osmolality when reconstituted with human milk due to further hydrolysis by human milk amylase. Based on the DE values for carbohydrates, one skilled in the art can readily select the carbohydrate source or combination of carbohydrates that will result in the preferred osmolality of the reconstituted fortifier powder/human milk solution.

As stated above, viscosity is also a characteristic of carbohydrates. Viscosity of the reconstituted fortifier powder/human milk solution plays a role in suspending the insoluble minerals during feeding. While higher viscosity's tend to reduce insoluble mineral fallout, the higher viscosity can cause tube/nipple clogging. A clogged feeding tube in a continuous feeding apparatus requires additional attention by the nursing staff who will have to unclog the tube, reset the pump system which may require a new preparation of fortified human milk. More importantly, a clogged tube prevents the timely delivery of much needed nutrients to a premature infant. The viscosity of the reconstituted fortifier powder/human milk solution of the instant invention is typically less than about 30 cps, preferably from about 10 cps to about 20 cps. Viscosity is inversely related to osmolality. The more hydrolyzed a starch is (higher DE), the lower the viscosity and the higher the osmolality. Based on the DE values for carbohydrates, one skilled in the art can readily select the carbohydrate source or combination of carbohydrates that will drive the viscosity and osmolality characteristics of the reconstituted fortifier powder/human milk solution to the preferred levels.

The fourth component of the fortifier powder of the present invention typically includes supplemented vitamins and minerals.

The preterm infant requires the electrolytes sodium, potassium and chloride for growth and for acid-base balance. Sufficient intakes of these electrolytes are also needed for replacement of losses in the urine and stool and from the skin. Calcium, phosphorus and magnesium are needed for proper bone mineralization. For bones to grow, adequate amounts of these minerals must be present in a feeding. LBW infants may develop rickets or osteopenia if they do not receive adequate amount of calcium and phosphorus in their diet. Phosphorus and magnesium are also found in intracellular fluid. These minerals are needed for the growth and function of soft tissue. Human milk does not provide enough calcium or phosphorus, even if these minerals were to be totally absorbed and retained, which they are not.

Trace minerals are associated with cell division, immune function and growth. Consequently, provision of sufficient amounts of trace minerals is needed for rapid growth in LBW infants. Human milk does not provide sufficient amounts of the trace minerals, especially zinc and copper, to meet the needs of a growing LBW infant. Another trace mineral, iron, is important for the synthesis of hemoglobin, myoglobin and iron-containing enzymes. However, it is not certain that LBW infants need the recommended amounts of iron during the first 2 months of life. The anemia of prematurity occurring shortly after birth cannot be avoided by giving supplemental iron. Also, the preterm infant is estimated to have sufficient iron stores without receiving iron supplementation, if blood loss is small, until 2 months of age. Consequently, the powdered human milk fortifier of the instant invention is low in iron. Zinc is needed for growth, for the activity of numerous enzymes, and for DNA, RNA and protein synthesis. Copper is necessary for the activity of several important enzymes. It is estimated that about 75% of the copper in a term neonate is accumulated during the last 10 to 12 weeks in utero. Consequently, LBW infants, especially those born weighing less than 1500 gm, are likely to have low copper stores. Manganese is needed for the development of bone and cartilage and is important in the synthesis of polysaccharides and glyoproteins.

LBW infants are likely to need more of most vitamins than provided by human milk alone because of low vitamin stores at birth, low intake of feedings, poor absorption of vitamins and clinical conditions requiring increased vitamin intakes.

Vitamin A is a fat-soluble vitamin essential for growth, cell differentiation, vision and the immune system. The vitamin A stores in LBW infants are adequate shortly after birth but decrease soon thereafter. Therefore, preterm infants may require higher intakes of vitamin A than term infants. Vitamin D is important for absorption of calcium and to a lesser extent, phosphorus, and for the development of bone.

For many years it was thought that poor bone development observed in LBW infants was due to insufficient vitamin D intake and metabolism and the LBW infants required significantly greater vitamin D intake than term infants. It is now recognized that calcium and phosphorus intakes are more important than vitamin D for bone growth in preterm infants. Vitamin E (tocopherol) prevents peroxidation of polyunsaturated fatty acids in the cell, thus preventing tissue damage. LBW infants may develop hemolytic anemia and vitamin E deficiency when fed feedings low in vitamin E and high in iron and polyunsaturated fatty acids. Additionally, preterm milk contains very low levels of vitamin K.

As are several other water-soluble vitamins, vitamin C is low in mature preterm milk. Folic acid is important in amino acid and nucleotide metabolism. Serum folate concentrations have been shown to fall below normal after 2 weeks of age in LBW infants with low folic acid intakes. Additionally, several B vitamins are present at low concentrations in preterm milk.

As described above, the variability of human milk vitamin and mineral concentrations and the increased needs of the preterm infant requires a minimal fortification to insure that a developing premature infant is receiving adequate amounts of vitamins and minerals while not over fortifying and possibly causing, for example, hypercalcemia. Using the recommendations of the Committee on Nutrition, American Academy of Pediatrics, one skilled in the art can readily calculate how much of a vitamin or mineral source should be added to the nutritional product in order to deliver the desired amount of a vitamin or mineral. (Nutritional needs of premature infants, PEDIATRIC NUTRITION HANDBOOK, ed. 4. Elk Grove Village, Ill. American Academy of Pediatrics, 1998, pp. 55–87) Practitioners also understand that appropriate additional amounts of vitamin and mineral ingredients need to be provided to nutritional compositions to compensate for some loss during processing and storage of such compositions.

Examples of supplemental vitamins and minerals in the fortifier powder of the instant invention typically include vitamin A, vitamin $B_1$, vitamin $B_2$, vitamin $B_6$, vitamin $B_{12}$, vitamin C, vitamin D, vitamin E, vitamin K, biotin, folic acid, pantothenic acid, niacin, m-inositol, calcium, phosphorus, magnesium, zinc, manganese, copper, sodium, potassium, chloride, iron and selenium. The additional nutrients chromium, molybdenum, iodine, taurine, carnitine and choline may also require supplementation. Desirably, the fortifier powder will include the natural form of vitamin E (RRR-d-alpha-tocopherol acetate).

The inventors discovered that the solubility characteristics of some of the minerals, particularly calcium, in the fortifier powder negatively impact protein stability in the fortified human milk solution. Specifically, the presence of soluble divalent minerals in the final product destabilizes both human milk protein and fortifier protein which causes the protein to precipitate out of solution and cling to the sides of the mixing containers. Experiment II evaluates protein denaturation by fortifier powder containing soluble calcium and the fortifier powder of the instant invention containing insoluble calcium. The inventors have tested the residue left on the sides of the mixing containers for protein and found the residue to consist of immunologically active whey and casein protein and other unidentified protein. Further, the inventors were able to calculate the percent of total protein lost as residue clinging to the sides of the mixing containers for each fortifier powder. Addition of fortifier powder containing soluble calcium to human milk resulted in the lose of 6% of the total protein in the fortified human milk. Protein losses this high can have a negative impact on the growth of preterm infants.

Conventional wisdom dictates that a soluble calcium source will maximize mineral bioavailabilty characteristics for a growing infant. This is supported by the incorporation of soluble calcium sources calcium gluconate and calcium glycerophosphate in the commercially available fortifier powder, Enfamil® Human Milk Fortifier. However, it is known that soluble divalent minerals, particularly calcium, are capable of interacting with proteins. The destabilization of proteins results in denatured protein that precipitates out of solution or clings to the sides of the reconstitution/delivery container. Consequently, the protein is not actually delivered to the infant which contribute to the slower growth rates (see Experiment III).

The current invention uses insoluble calcium sources and addresses the resulting mineral precipitation issues first by making the fortifier a powder and secondly by using particle sizes small enough (ultra micronized) to stay in solution during feeding. Examples of suitable insoluble calcium sources typically include calcium phosphate dibasic, calcium phosphate tribasic and calcium carbonate and calcium citrate. Alternatively, the calcium is in a colloidal suspension with the protein such as calcium caseinate.

Preferably, about 95% of the total calcium is supplied by calcium phosphate tribasic and about 5% of the total calcium is supplied by calcium citrate.

Numerous commercial sources for insoluble calcium are readily available and known to one practicing the art. For example, calcium phosphate tribasic, calcium phosphate dibasic, calcium citrate are available from Mallinckrodt Specialty Chemicals in Charlotte, N.C. Calcium carbonate is available from Prillaman Chemical Corporation in Suffolk, Va. Calcium caseinate is available from New Zealand Milk Products in Hamilton, New Zealand.

The incorporation of insoluble calcium in the fortifier powder leads one skilled in the nutritional arts to be concerned about bioavailability of the calcium for this growing premature population. Preterm human milk is already deficient in calcium and if the fortifier powder provides calcium in a form that is not bioavailable to the preterm infant, growth will be negatively impacted. The inventors performed preliminary studies (Experiment IV) evaluating the forearm bone density of infants supplemented with the fortifier powder of the instant invention containing insoluble calcium and compared their forearm bone density to infants supplemented with fortifier powder containing soluble calcium. Surprisingly, the results show no difference in bone density. The addition of insoluble calcium sources to the fortifier powder of the instant invention prevented the denaturation of protein in the fortified milk and was absorbed by the premature infant. Consequently, the protein and calcium were successfully delivered to the premature infant and the infant was able to thrive and grow.

The nutritional powder of this invention can be manufactured using techniques well known to those skilled in the art. While manufacturing variations are certainly well known to those skilled in the nutritional formulation arts, a few of the manufacturing techniques are described in detail in the Examples. Generally speaking an oil blend is prepared containing all oils, any emulsifier, and the fat soluble vitamins. Two more slurries (carbohydrate and protein) are prepared separately by mixing the carbohydrate and minerals together and the protein in water. The two slurries are then mixed together with the oil blend. The resulting mixture is homogenized, heat processed, standardized with water soluble vitamins, and dried. The resulting powder may be milled to a specific particle size and/or aggolmerized to modify particle size and mixability characteristics. Those skilled in the nutritional formulation arts would also be able to dry blend the individual starting materials and add the liquid ingredients through agglomeration or during the dry blending step.

Individual unit dose size packages are preferred over bulk packaging. Because of the small volumes of milk administered to premature infants over the course of a days feeding, small volumes of fortified human milk are prepared. Powder sterility in a bulk container that has been repeatedly opened, powder scooped out, recovered and stored is always a concern in a hospital environment. Individual unit doses allow for addition of small amounts of powder to human milk without the possibility of contamination of the remaining powder since all of the powder is used in a single preparation. As noted above, the unit dose of the invention typically is the amount of from about 0.5 gm to about 10 gm of fortifier powder in a unit dose, preferably from about 0.8 gm to about 5.0 gm of powder in a unit dose, more preferably from about 0.85 gm to about 2.0 gm of powder in a unit dose. Depending on the volume of a days feeding, from about 1 to about 4 unit doses will be added to about 25 ml to about 100 ml, respectively.

Numerous types of containers are readily available and known to one practicing the art. Examples of container types typically include packets or sachets which may be manufactured of paper, foil and plastic film, and foil and plastic film coated paper; and ampoules which may be manufactured of plastic, reinforced paper and glass.

As stated above, the instant invention also relates to a method of providing nutrition to preterm infants by adding the fortifier powder of the instant invention to human milk and administering the fortified human milk to a premature infant. The invention further provides a method of promoting growth of a premature infant by administering the fortified human milk to a premature infant. Experiments III and IV describe the study protocol and better growth of premature infants with the fortifier powder of the instant invention compared to a commercially available fortifier powder.

The invention also relates to a method for enhancing the emulsion stability of human milk by adding an emulsifier to the human milk. Surprisingly, the emulsifier helps to prevent the separation of fat globules in human milk. The inventors discovered that the addition of the small amount of emulsifier in the fortifier powder to human milk improved phase separation results. The study and results comparing the physical stability of human milk and fortifier powder/human milk are described in Experiment I. The amount of emulsifier in the fortified human milk solution will typically be present in from about 0.36 wt/vol % to about 3.6 wt/vol % of the human milk solution, preferably from about 0.54 wt/vol % to about 1.8 wt/vol % of the human milk solution.

MANUFACTURING EXAMPLE A

A batch of fortifier powder is manufactured by combining the appropriate ingredients to generate one carbohydrate/mineral (CHO/MIN) slurry, one oil blend and one protein in water slurry(PIW). The CHO/MIN, oil blend and PIW slurries are mixed together to form the final blend. The final blend is then processed with an HTST treatment. After standardization, the final blend is spray dried.

Table 2 presents a bill of materials for manufacturing 8,172 kg of powdered human milk fortifier. A detailed description of its manufacture follows.

TABLE 2

Bill of materials

| Ingredient | Amount |
|---|---|
| Ingredient water | 16,205 L |
| Corn syrup solids | 1603 kg |
| Magnesium chloride | 96.2 kg |
| Potassium citrate | 223.8 kg |
| Sodium citrate | 6.6 kg |
| Sodium chloride | 15.4 kg |
| MCT oil | 801 kg |
| Lecithin | 16.6 kg |
| Vitamin A | 2.36 kg |
| Vitamin D | 359.3 g |
| Vitamin K | 27.5 g |
| Natural Vitamin E | 7.6 kg |
| Calcium carbonate | 33.1 kg |
| Tricalcium phosphate | 646 kg |
| Whey protein concentrate | 1506 kg |
| Non fat dry milk | 3307 kg |
| potassium citrate | 257.2 g |
| ferrous sulfate | 3.7 kg |
| Zinc sulfate | 11.1 kg |
| Copper sulfate | 1.84 kg |
| Manganese sulfate | 0.320 kg |
| Sodium selenate | 0.001 kg |
| Niacinamide | 0.98 kg |
| Riboflavin | 1.14 kg |
| Calcium pantothenate | 4.08 kg |
| Pyridoxine hydrochloride | 0.655 kg |
| m-inositol | 9.55 kg |
| Biotin | 0.0727 kg |
| Folic acid | 0.0775 kg |
| Cyanocobalamin | 0.0016 kg |
| Ascorbic acid | 153.5 kg |

A carbohydrate/mineral slurry is prepared by heating 2,763 liters of ingredient water to 54° C.–62° C. With agitation, the specified amounts of corn syrup solids (Maltrin M200 distributed by Grain Processing Corporation, Muscatine, Iowa), magnesium chloride, sodium chloride, sodium citrate, potassium citrate, ultra micronized tricalcium phosphate and calcium carbonate are added to the heated water. The slurry is held under agitation at 54° C.–62° C. for not longer than six hours until it is blended with the other slurries.

An oil blend is prepared by heating the specified amount of MCT oil (distributed by Stepan, Maywood, N.J.) to 32° C.–37° C. with agitation. An emulsifier (standard fluid lecithin distributed by Central Soya, Ft. Wayne, Ind.) is then added under agitation and allowed to dissolve. Vitamin A,D,K and Natural Vitamin E (distributed by Vitamins, Inc., Chicago, Ill.) are then added to the slurry with agitation. The completed oil slurry is held under moderate agitation at a temperature from 26° C. to 48° C. for a period of no longer than six hours until it is blended with the other slurries.

A protein-in-water slurry is prepared by heating 9,053 liters of ingredient water to 48° C.–60° C. With agitation, the specified amount of whey protein concentrate (AMP 800 distributed by AMPC, Inc. Ames, Iowa) and nonfat dry milk is added to the heated water. The completed protein-in-water slurry is not held but blended directly with the other slurries.

The protein-in-water, oil blend and carbohydrate/mineral slurries are blended together with agitation and the resultant blend is maintained at a temperature from 51° C. to 60° C. After waiting for at least five minutes with agitation the final blend pH is adjusted with 1N KOH to a pH from 6.45 to 6.80. The total solids of the final blend is 30%. The final blend is held for no longer than two hours after the pH check.

After waiting for a period of not less than five minutes nor greater than two hours, the blend is subjected to deaeration, high-temperature-short-time heat treatment, and homogenization, as follows:

A. deaerate the blend at 10–15 inches Hg;
B. emulsify the blend at 900–1100 psig in a single stage homogenizer;
C. pass the blend through a plate/coil heater and heat the mix to 71° C. to 82° C.;
D. homogenize the blend at 3900 to 4100/400 to 600 psig in a double stage homogenizer;
E. pass the blend through a 16 second hold tube at a temperature from 73° C. to 85° C.;
F. cool the blend to a temperature from 1° C. to 7° C.; and
G. store the blend at a temperature from 1° C. to 7° C.

After the above steps have been completed, appropriate analytical testing for quality control is conducted. Based on the analytical results of the quality control tests, batch corrections are made if need be. Final blend total solids are from 29% to 31%.

A water soluble vitamin solution, ascorbic acid solution and trace mineral solution are prepared separately and added to the processed blend.

The ascorbic acid solution is prepared by adding the required amount of ascorbic acid to 2,453 liters of 10° C. to 37° C. water with agitation.

The mineral solution is prepared by heating 321 liters of ingredient water to 37° C. to 65° C. Under agitation, add the required amount of potassium citrate and ferrous sulfate. Allow to agitate until the solution is a clear green color. Add the required amounts of zinc sulfate, copper sulfate, manganese sulfate and sodium selenate to the green mineral solution. Agitate five minutes minimum.

The water soluble vitamin solution is prepared by heating 530 liters of ingredient water to 37° C. to 65° C. The required quantities of niacinamide, riboflavin, calcium pantothenate, pyridoxine hydrochloride, thiamine hydrochloride, m-insitol, biotin, folic acid and cyanocobalamin are added to the heated water.

All of the ascorbic acid solution, the mineral solution and water soluble vitamin solution is then added to the blended slurry under agitation.

The final mix is preheated through a plate heater to 71° C.–82° C. before going to a surge tank. The mix leaves the surge tank and passes through the steam injector where it is heated to 88° C.–93° C. The mix enters the vapor-flash chamber where it is cooled to 71° C.–82° C., then pumped through an in-line 200 micro filter prior to the high pressure pump and into the dryer. The dryer settings are as follows:

| Nozzle pressure | 3000–5000 psig |
| Liquid flow rate | 11 gpm max. |
| Ingoing Air Temperature | 160° C.–207° C. |
| Outgoing Air Temperature | 82° C.–108° C. |

To control bulk density, dispersibility, particle size, moisture and physical stability, the specific spray nozzle, nozzle pressure, drying temperatures and fine reinjection parameters may vary depending upon the drying conditions of the day. The powder passes from the dryer into the powder cooler where the powder is cooled to below 43° C. The cooled powder is stored in appropriate containers until being filed in individual packets.

EXPERIMENT I

The objective of the study was to evaluate the emulsion stability of human milk after the addition of the fortifier powder of the instant invention. The emulsion stability of liquids which incorporate powders is routinely tested by a phase separation test. The test evaluates the separation of human milk into fat-soluble and water-soluble layers. 7.2 gm of fortifier powder produced as in Manufacturing Example A was weighed into small plastic cups and covered to keep dry. Using a 250 mL graduated cylinder, 200 ml of human milk was poured into a 500 mL beaker. The fortifier powder was slowly added to the beaker while stirring vigorously. Stirring continued for about 30 seconds to ensure the powder was thoroughly hydrated. The solution was immediately transferred to a 250 mL graduated cylinder for phase separation test. The sample sat undisturbed for 30, 60 and 120 minutes before analysis. The sample was evaluated for any evidence of a fat layer at the top. A high intensity flashlight was held against the gradated cylinder to help distinguish between foam and fat layer. In addition, a small spatula was placed inside the cylinder to push on the edge of the top layer to help determine if the top layer is foam or fat layer. The fat layer was read directly off the graduated cylinder in ml. Table 3 lists the phase separation results for the human milk/fortifier powder solution and the human milk control after 30, 60 and 120 minutes.

TABLE 3

Phase Separation Results

| Sample | 30–60 min | 120 min |
| --- | --- | --- |
| fortified human milk | 1 ml | 1 ml |
| human milk control | 2 ml | 2 ml |

The fat in the human milk control sample separated and rose to the top of the solution as demonstrated by a 2 ml fat layer. The fortified human milk had half as much fat separate and rise to the top of the solution as demonstrated by a 1 ml fat layer. Human milk fat is known to separate and adhere to the sides of feeding containers and result in significant loss of fat (energy). The small amount of emulsifier added to the fortifier powder to help the powder incorporate into the human milk was surprisingly also able to decrease the fat separation observed in human milk, thereby delivering more calorically dense fat to the premature infant.

As discussed above, fat is crucial for growth of premature infants. The lose of fat helps explain the difference in growth observed in preterm infants supplemented with the commercially available powdered human milk fortifier which does not contain an emulsifier and the powdered human milk fortifier of the instant invention which contains an emulsifier. (See Experiment III and IV)

EXPERIMENT II

Reports from the NICUs described a residue that clung to the walls of the reconstitution container when the commercially available fortifier powder was added to human milk and there were concerns that the infants were not actually receiving all the nutrients in the fortified milk. The residue was examined under the electron microscope and was found to be protein.

The objective of the study was to quantify and identify the protein residue left on the side of the reconstitution containers of powdered human milk fortifier containing soluble calcium (SC) and the powdered human milk fortifier of the instant invention containing insoluble calcium (IC). The powdered human milk fortifier containing soluble calcium sample was the Enfamil® Human Milk Fortifier the composition described in Table 1. The powdered human milk fortifier containing insoluble calcium sample was the fortifier powder of the instant invention produced as described in Manufacturing Example A.

Samples of each powdered human milk fortifier were reconstituted by adding 0.9 g of the appropriate powder to 25 mL of 2% milk in a glass graduated cylinder. The 2% milk control contained only 25 mL of milk, but was otherwise treated in an identical manner. Each graduated cylinder was then covered, and given 6 vigorous shakes to facilitate powder reconstitution. Each solution was then poured into a labeled beaker for protein analysis. Each graduated cylinder was then inverted onto a paper towel and allowed to drain for 1 minute and then set upright. 10.0 mL of Universal Assay Buffer (PBS containing 0.1% Tween 20 and 0.05% ovallbumin) was added, and the cylinder was covered. The inside walls of the cylinder were rinsed by shaking to get particulates off the side walls and into the buffer solution. To facilitate solubilization of the residue, each cylinder was then incubated for 15 minutes in a water bath at 37° C., then allowed to cool to room temperature prior to further dilution in buffer.

To evaluate the type of protein in the residue an ELISA analysis was used to quantitate immunologically active casein and whey protein. In the casein and whey ELISA analysis, samples were tested undiluted, and at subsequent 4 fold dilutions up to and including a dilution of 1 to 262,144. The enzyme-linked immunosorbent assay (ELISA) method utilized is described in the article by Cordle et al. (Evaluation of the Immunogenicity of protein hydrolysate formulas using laboratory animal hyperimmunization. PEDIATRIC ALLERGY AND IMMUNOLOGY (5) p.14 –19, 1994). The ELISA assay is designed for the detection and quantitation of immunologically active casein or whey using rabbit anti-whey antibody and rabbit anti-casein antibody.

This assay measures only the immunologically active casein and whey protein components in the residue. Results of the ELISA analyses for two separate reconstitutions (A and B) of each powdered human milk fortifier are shown in Table 4 below.

TABLE 4

ELISA analysis of residue for immunologically active casein and whey protein

| Sample | Total mg casein | Total mg whey |
|---|---|---|
| 2% milk control | 1.31 | 0.31 |
| IC-A | 2.55 (1.24) | 1.89 (1.58) |
| IC-B | 3.49 (2.18) | 2.32 (2.01) |
| SC-A | 4.98 (3.67) | 3.51 (3.20) |
| SC-B | 5.77 (4.46) | 4.94 (4.63) |

IC-fortifier powder of the instant invention containing insoluble calcium
SC-Enfamil ® Human Milk Fortifier containing soluble calcium
(value) corrected for control contribution All samples left immunologically active casein and whey protein on the walls of the reconstitution container. However, the SC fortifier powder left 137% more casein and 118% more whey protein behind on average than the IC fortifier powder of the instant invention when corrected for contribution of the control.

To evaluate the amount of protein lost in the residue, the amount of total protein in each sample must be determined. First, the quantity of protein in solution is determined. The solution which was poured from the graduated cylinder in the preparation step above was analyzed by the TECATOR KJELTEC AUTO 1030 system for nitrogen to determine the quantity of protein that did not adhere to the reconstitution container (the protein in solution).

The TECATOR KJELTEC AUTO 1030 system (Perstorp Analytical, Inc.) is an integrated, semi-automated nitrogen analyzer which uses an adaptation of the classical acid digestion/ammonia distillation procedure first described by Johann Kjeldahl in 1883. The operating manuals for the Kjeltec Auto 1030 System were followed to determine the amount of nitrogen in the samples.

The amount of protein in the sample is calculated, based on the nitrogen concentration. The nitrogen concentrations in various proteins are known, and empirically-determined conversion factors is used to convert from % nitrogen to % protein. For example, milk proteins contain, on the average, 15.67% nitrogen; thus, for milk proteins, $$\% \text{ Protein} = \% \text{ Nitrogen} \times (100\% \text{ Protein}/15.67\% \text{ Nitrogen})$$

or $$\% \text{ Protein} = \% \text{ Nitrogen} \times 6.38$$

Using the percent protein data and the known reconstitution volume (25 mL) the total protein that did not adhere to the sides of the container can be calculated. The amount of protein that did not adhere to the sides of the reconstitution container for each sample is shown in Table 5 below.

TABLE 5

Amount of total protein that did not adhere to the sides of the reconstitution container

| Sample | mg protein/ml | total mg protein |
|---|---|---|
| 2% milk control | 34.2 | 855 |
| IC-A | 43.4 (9.2) | 1,085 (230) |
| IC-B | 43.4 (9.2) | 1,085 (230) |
| SC-A | 39.7 (5.5) | 992.5 (137.5) |
| SC-B | 39.6 (5.4) | 990 (135) |

IC-fortifier powder of the instant invention containing insoluble calcium
SC-Enfamil ® Human Milk Fortifier containing soluble calcium
(value) corrected for control contribution The total mg of protein in solution for the SC sample is 136.25 mg on average and the total mg of protein in solution for the IC sample is 230 mg on average. These differences are expected as each fortifier powder contributes different levels of protein to the milk solution. These values are utilized below to calculate the percent total protein lost as residue on the side of the reconstitution container.

The protein residue was tested for immunologicaly active whey and casein above. However, there could be additional protein present in the residue that would be detected. So, the total protein concentration of the residue was measured by the isoabsorbance method described in a publication by Ehresmann et al. (Spectrophotometric determination of protein concentration in cell extracts containing tRNA's and rRNA's, ANALYTICAL BIOCHEMISTRY (54) p. 454–463, 1973). A single reconstitution of each of the formulas and the milk control were prepared as previously described, except that the residue was dissolved in 10.0 mL of PBS. Isoabsorbance measures all protein present, and cannot differentiate among protein components. The results are shown in the Table 6 below.

TABLE 6

Amount of total protein in the residue of the reconstitution container

| Sample | mg protein/ml | total mg protein |
|---|---|---|
| 2% milk control | 0.45 | 4.5 |
| IC | 0.9 (0.45) | 9 (4.5) |
| SC | 1.37 (0.92) | 13.7 (9.2) |

IC-fortifier powder of the instant invention containing insoluble calcium
SC-Enfamil ® Human Milk Fortifier containing soluble calcium
(value) corrected for control contribution By this technique, additional protein that was not detected by the ELISA method was found in the residue. The SC fortifier powder sample left 104% more total protein behind than the IC fortifier powder of the instant invention when corrected for contribution of control.

Using the estimate of the protein which did not adhere to the walls of the reconstitution container above, and the value for the total protein measured in the residue, a percent of protein lost can be generated for each sample. Table 7 lists the total protein lost in the residue clinging to the reconstitution container.

TABLE 7

Total protein lost in the reconstitution container

| Sample | Residue/total protein × 100 | Protein lost in residue |
|---|---|---|
| 2% milk control | (4.5/855 + 4.5)100 | 0.52% |
| IC-A | (4.5/230 + 4.5)100 | 1.9% |
| IC-B | (4.5/230 + 4.5)100 | 1.9% |
| SC-A | (9.2/137.5 + 9.2)100 | 6.3% |
| SC-B | (9.2/135 + 9.2)100 | 6.4% |

IC-fortifier powder of the instant invention containing insoluble calcium
SC-Enfamil ® Human Milk Fortifier containing soluble calcium
(value) corrected for control contribution The SC fortifier powder lost 6% or 234% more protein in the residue clinging to the sides of the container on average than the IC fortifier powder of the instant invention when corrected for contribution of control. Clearly, the presence of soluble calcium denatures the protein causing it to cling to the sides of the mixing containers and negatively impacts the amount of protein delivered to the premature infant.

As discussed above, protein is crucial for growth of premature infants. The lose of protein helps explain the difference in growth observed in preterm infants supplemented with the commercially available powdered human milk fortifier containing soluble calcium and the powdered human milk fortifier of the instant invention containing insoluble calcium. (See Experiment III and IV)

EXPERIMENT III

The primary objective of the study was to demonstrate that the fortifier powder of the instant invention added to human milk (HM) would support acceptable growth in preterm infants. A second objective was to evaluate the serum biochemistries (ie, protein status, calcium, alkaline phosphatase), tolerance, clinical problems, and morbidity of premature infants consuming the nutritional module. Another secondary objective was to compare the nutritional powder of the instant invention to a commercial fortifier powder that has been in use for a number of years.

An intent-to-treat, prospective, randomized, double-blinded multicenter study was conducted to evaluate preterm infants receiving preterm milk supplemented with either a commercially available powdered human milk fortifier (Enfamil® Human Milk Fortifier, control) or the fortifier powder of the current invention(experimental) at every feeding. Subjects were enrolled and randomized to each fortifier powder prior to 21 days of life. Study Day 1 was when fortification of the study fortifier powder had begun and the subject reached an intake of at least 100 mL/kg/day. Anthropometric indices, serum biochemistries, intake, tolerance, and morbidity data were assessed. Each infant was studied until hospital discharge; only anthropometric variables (weight, length, and head circumference) were collected after Study Day 29.

Premature infants were recruited from neonatal intensive care units that had agreed to collaborate with study investigators located in Salt Lake City, Utah; Houston, Tex.; Indianapolis, Ind.; Kansas City, Mo.; Louisville, Ky.; and Omaha, Nebr.

Single, twin, or triplet infants born ≦33 weeks gestational age, with appropriate weight for gestational age, and weighing ≦1600 g were eligible to participate. One-hundred and forty-four infants were randomized to either control or experimental; 70 preterm infants were randomized to the control group and 74 preterm infants were randomized to the experimental group. The randomization was proportional for birth weight (≦1100 g and ≦1100 g) and gender.

The nutrient content of the two powder fortifiers added to human milk is listed in Table 8.

TABLE 8

Nutrient Content of Human Milk, control and experimental fortifiers

| Nutrients | Preterm Milk-Mature* (per 100 mL) | control† (per 3.8 g) | experimental‡ (per 3.6 g) | |
|---|---|---|---|---|
| | | | Batch 1 | Batch 2 |
| Energy, kcal/ml | 67 | 14 | 13.8 | 14 |
| Protein, g | 1.4 | 0.7 | 1.0 | 1.0 |
| source | mature human milk | whey protein concentrate/ sodium caseinate | whey protein concentrate/ nonfat dry milk | whey protein concentrate/ nonfat dry milk |
| Fat, g | 3.9 | <0.1 | 0.41 | 0.37 |
| source | mature human | none added | MCT oil | MCT oil |

TABLE 8-continued

Nutrient Content of Human Milk, control and experimental fortifiers

| Nutrients | Preterm Milk-Mature* (per 100 mL) | control† (per 3.8 g) | experimental‡ (per 3.6 g) |
|---|---|---|---|
| Carbohydrate, g | 6.6 | 2.7 | 1.6 | 1.7 |
| source | milk lactose | corn syrup solids | corn syrup solids | corn syrup solids |
| Vitamins | | | | |
| A, IU | 389 | 950 | 640 | 763 |
| D, IU | 2.0 | 210 | 134 | 145 |
| E, IU | 1.0 | 4.6 | 3.4 | 3.5 |
| K, mcg | 0.21§ | 4.40 | 8.50 | 8.60 |
| Thiamin (B-1), mg | 0.021§ | 0.151 | 0.270 | 0.300 |
| Riboflavin (B-2), mg | 0.048 | 0.210 | 0.460 | 0.500 |
| B-6, mg | 0.015 | 0.114 | 0.230 | 0.240 |
| B-12, mcg | 0.05§ | 0.18 | 0.85 | 0.83 |
| Niacin, mg | 0.15§ | 3.0 | 0.40 | 0.42 |
| Folic acid, mcg | 3.3 | 25 | 30 | 27 |
| Pantothenic acid, mg | 0.18§ | 0.73 | 1.60 | 1.40 |
| Biotin, mcg | 0.4 | 2.7 | 30.0 | 33.0 |
| C, mg | 11 | 11.6 | 23.3 | 60.0 |
| Minerals | | | | |
| Calcium, mg | 25 | 90 | 131 | 118 |
| Phosphorus, mg | 13 | 45 | 68 | 67 |
| Magnesium, mg | 3.2 | 1.0 | 7.7 | 7.7 |
| Zinc, mg | 0.34 | 0.71 | 1.30 | 1.2 |
| Manganese, mcg | 0.6 | 4.7 | 9.2 | 12.0 |
| Copper, mg | 0.064 | 0.062 | 0.200 | 0.200 |
| Sodium, mg | 25.0 | 7.0 | 17.5 | 17.5 |
| Potassium, mg | 57 | 15.6 | 72.0 | 72.0 |
| Chloride, mg | 55.0 | 17.7 | 40.0 | 40.0 |
| Iron, mg | 0.12 | — | 0.35 | 0.45 |
| Selenium, μg | 2.3 | — | 1.4 | 0.99 |

†Amounts added to each 100 mL human milk (4 packets of fortifier powder). Values are label claim.
‡Amounts added to each 100 mL milk (4 packets of fortified powder). Values are analyzed values. Two batches were manufactured for use in the study.
§Values for mature human milk were used.

The independent variables (treatments) were the control fortifier powder and the experimental fortifier powder which were added to HM. Both fortifiers were provided in small packets in powdered form and were added to 25 mL HM.

The primary outcome variable was weight gain (g/kg/day) from study day 1 to study day 29 or discharge, whichever came first. Secondary outcome variables were length gain (mm/day) and serum biochemistries to evaluate protein status, electrolyte status, mineral homeostasis, and vitamin A and E status. Serum biochemistries also included unscheduled laboratory results recorded in the medical chart. Tertiary variables included head circumference gain (mm/day), clinical history, intake, tolerance, clinical problems/morbidity, respiratory status, antibiotic use, and the number of transfusions.

Mean total energy intakes during the study period was not different between the two groups. Infants fed control fortified human milk received 118.0±2.2 kcal/kg/day while the infants fed experimental fortified human milk received 118.0±1.6 kcal/kg/day. There was a difference in mean protein intake between the two groups. Infants fed control fortified human milk received 3.1±0.1 g protein/kg/day while infants fed experimental fortified human milk received 3.5±0.1 g protien/kg/day which is consistent with the slightly higher protein content of experimental fortifier powder.

There were consistent differences among infants in the two fortifier powder groups with respect to growth (weight, length, head circumference) with the control group always growing more slowly. The significant difference in weight gain for the primary analysis between the groups was 2.6 g/kg/day (experimental>control; p<0.0005). The significant difference in length gain for the primary analysis between the groups was 0.2 mm/day (experimental>control; p<0.05). Although the primary analysis for head circumference gain was not different between the groups, there was a significant difference in head circumference gain of 0.15 mm/day when analyzed from study day 1 to last fortifier powder feeding (experimental>control; p<0.05). Furthermore, the differences in weight, length, and head circumference gains between the groups were even greater in the evaluable group of infants than in the intent-to-treat group of infants. The significant differences in weight, length, and head circumference gains (p<0.0005; p<0.05; and p<0.001, respectively) for the primary analyses were 4.07 g/kg/day, 0.23 mm/day, and 0.30 mm/day, respectively, with the control group growing more slowly.

The differences in serum biochemistries between the groups were also very consistent between the intent-to-treat and evaluable groups. Of most clinical significance were the mean alkaline phosphatase and calcium values. In the intent-to-treat group, mean alkaline phosphatase values among infants randomized to the experimental group appeared to be higher compared to the infants randomized to the control group (327 U/L vs 272 U/L, respectively); however, mean values for both groups were decreased by study day 29. In addition, mean alkaline phosphatase was in the normal range for both groups. Results were similar in the evaluable group. In contrast, in the intent-to-treat group, the mean serum calcium values among infants fed control fortifier powder tended to be higher overall than among infants fed experimental fortifier powder (p=0.069). As expected, in the evaluable group the overall differences were greater with mean calcium values of 11.2 mg/dL in the control group and 10.3 mg/dL in the experimental group(p=0.016). A value greater than 11 mg/dL is considered in the upper range and is suggestive of hypercalcemia.

There were no significant differences between the groups in respect to clinical problems or morbidity data. Overall tolerance to both products was excellent. The only difference was in the episodes of vomiting with the control group having a greater number (percent) of days with vomiting episodes than the experimental group (18% vs 11%; p<0.01). The control group also had a statistically greater number of infants who exited early from the study for reasons of gastric residuals and/or abdominal distention than did the experimental group (6 vs 0; p=0.012).

The primary findings of this study suggest that increases in protein, the addition of fat and emulsifier and use of insoluble calcium in the fortifier powder of the instant invention results in dramatic improvements in growth performance of low-birth-weight infants even though the caloric density has not been changed.

EXPERIMENT IV

The experiments above each describe the positive benefits of using insoluble calcium as the calcium source of choice in the fortifier of the instant invention. Less protein is left behind in the mixing containers which shows positive benefits in premature infant growth. However, bone mineralization is a concern with the use of insoluble calcium.

The objectives of this study were similar to those in Experiment III. A preliminary evaluation of mineral bioavailability, specifically calcium, of the fortifier powder of the instant invention was added to the protocol through documentation of forearm bone density of premature infants supplemented with the fortifier powder of the instant invention which contains insoluble calcium. These forearm bone density values were compared to those of premature infants supplemented with a commercially available fortifier powder which contains soluble calcium.

The protocol was as described in Experiment III. A prospective, randomized, double-blinded study was conducted to evaluate preterm infants receiving their own mother's milk supplemented with either a commercial powdered human milk fortifier containing soluble calcium (Enfamil® Human Milk Fortifier, control) or the fortifier powder of the instant invention containing insoluble calcium (experimental) at every feeding. Anthropometric indices, serum biochemistries and forearm's bone density, fat and lean mass were studied at days 1,15 and 29. Infant's forearm was scanned using the dual x-ray absorption method.

Single, twin, or triplet infants born ≦33 weeks gestational age, with appropriate weight for gestational age, and weighing ≦1500 g were eligible to participate. Forty-three infants were randomized to either control or experimental.

On day one, there were no differences between control and experimental groups in weight, length, head circumference or forearm's bone density, fat and lean mass.

Mean total energy intakes during the study period were similar (110±15 vs 114±9 kcal/dg/d). However, there was a significant difference in weight gain between the groups, 18±2 vs 15±3 g/kg/day (experimental>control; p=0.0003). There were no differences in length or head circumference gains between the two groups and the serum biochemistries were similar between the groups. By day 15, the experimental group had a higher lean mass than controls 16±3 gm vs 14±3 gm (p<0.05).

Bone mineral content (0.608±0.172 vs 0.631±0.175 g/cm) and fat mass (6.9±3.3 vs 7.5±3.7 gm) were similar during the study.

These findings suggest that the insoluble calcium of the fortifier powder of the instant invention was as available as the soluble calcium of the control fortifier powder. Additionally, the growth findings of this study are consistent with the results from the previous study. These findings suggest that the fortifier powder of the instant invention provides higher weight gain in preterm infants than a commercial fortifier powder and suggest that the weight gain may be from higher lean mass gain.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention.

We claim:

1. A powdered human milk fortifier comprising:
   a. a protein component present in a quantity of from about 28 wt/wt % to about 42 wt/wt % of the powdered human milk fortifier,
   b. a fat component present in a quantity of from about 5 wt/wt % to about 30 wt/wt % of the powdered human milk fortifier wherein said fat component further comprises a source of medium chain triglycerides,
   c. a carbohydrate component present in a quantity of from about 28 wt/wt % to about 67 wt/wt % of the powdered human milk fortifier, and;
   d. at least one source of insoluble calcium.

2. The powdered human milk fortifier according to claim 1 which further comprises at least one source of iron.

3. A method of providing supplemental nutrients to preterm ipfants comprising adding the powdered human milk fortifier according to claim 1 to human milk and administering a fortified human milk to a premature infant.

4. A method for promoting growth of a premature infant comprising administering fortified human milk to a premature infant, said fortified human milk comprises:
   a. human milk, and
   b. the powdered human milk fortifier according to claim 1.

5. The method of providing supplemental nutrients according to claim 3, in which about 0.5 gm to about 10 gm of said fortifier is administerd per day.

6. A powdered human milk fortifier comprising:
   a. a protein component present in a quantity of from about 28 wt/wt % to about 36 wt/wt % of the powdered human milk fortifier,
   b. a fat component present in a quantity of from about 5 wt/wt % to about 20 wt/wt % of the powdered human milk fortifier wherein said fat component further comprises a source of medium chain triglycerides,
   c. a carbohydrate component present in a quantity of from about 44 wt/wt % to about 67 wt/wt % of the powdered human milk fortifier, and;
   d. at least one source of insoluble calcium.

7. The powdered human milk fortifier according to claim 6 which further comprises at least one source of iron.

8. A method of providing supplemental nutrients to preterm infants comprising adding the powdered human milk fortifier according to claim 6 to human milk and administering a fortified human milk to a premature infant.

9. The method of providing supplemental nutrients according to claim 8, in which about 0.5 gm to about 10 gm of said fortifier is administered per day.

10. A method for promoting growth of a premature infant comprising administering fortified human milk to a premature infant, said fortified human milk comprises:
   a. human milk, and
   b. the powdered human milk fortifier according to claim 6.

11. A fortified human milk comprising:
   a.) human milk, and
   b.) from about 0.008 wt/vol % to about 0.05 wt/vol % of a powdered human milk fortifier which comprises;

i.) a protein component present in a quantity of from about 28 wt/wt % to about 55 wt/wt % of the powdered human milk fortifier, ii.) a fat component p rsent in a quantity of from about 8wt/wt % to about 30 wt/wt % of the powdered human milk fortifier, iii.) a carbohydrate component present in a quantity of from about 15 wt/wt % to about 75 wt/wt % of the powdered human milk fortifier, and iv.) at least one source of insoluble calcium.

12. A method of providing supplemental nutrients to preterm infants comprising administering the fortified human milk according to claim 11 to a premature infant.

13. A method for promoting growth of a premature infant comprising administering the fortified human milk according to claim 11 to a premature infant.

* * * * *

UNITED STATES PATENT AND TRADEMARK OFFICE
CERTIFICATE OF CORRECTION

PATENT NO.    : 6,294,206 B1
DATED         : September 25, 2001
INVENTOR(S)   : Barrett-Reis et al.

It is certified that error appears in the above-identified patent and that said Letters Patent is hereby corrected as shown below:

Column 24,
Line 43, should read: term "ipfants" -- infants -- comprising adding the powdered human milk Column 25,
Line 18, should read: b.) from about "0.008" -- 0.8 -- wt/vol% to about "0.05" -- 5.0 -- wt/vol % of
Line 19, should read: a powdered human milk fortifier which comprises ";" -- : --

Column 26,
Line 4, should read: ii.) a fat component "p rsent -- present -- in a quantity of from about Signed and Sealed this Twenty-sixth Day of November, 2002

Attest:

JAMES E. ROGAN
Attesting Officer    Director of the United States Patent and Trademark Office